(12) United States Patent
Dassanayake et al.

(10) Patent No.: US 12,691,197 B2
(45) Date of Patent: Jul. 28, 2026

(54) GERMICIDAL LIGHTING FIXTURE USING PHOTOCATALYTIC OXIDATION

(71) Applicant: eLUMIGEN, LLC, Troy, MI (US)

(72) Inventors: Mahendra Dassanayake, Bloomfield Hills, MI (US); Brian Petku, Clarkston, MI (US)

(73) Assignee: eLUMIGEN, LLC, Troy, MI (US)

( * ) Notice: Subject to any disclaimer, the term of this patent is extended or adjusted under 35 U.S.C. 154(b) by 900 days.

(21) Appl. No.: 17/506,165

(22) Filed: Oct. 20, 2021

(65) Prior Publication Data

US 2022/0118149 A1     Apr. 21, 2022

Related U.S. Application Data

(60) Provisional application No. 63/093,859, filed on Oct. 20, 2020.

(51) Int. Cl.
*A61L 9/20*     (2006.01)

(52) U.S. Cl.
CPC .......... *A61L 9/205* (2013.01); *A61L 2209/111* (2013.01); *A61L 2209/12* (2013.01); *A61L 2209/134* (2013.01); *A61L 2209/14* (2013.01)

(58) Field of Classification Search
CPC ................. A61L 9/205; A61L 2209/12; A61L 2209/134; A61L 9/20
See application file for complete search history.

(56) References Cited

U.S. PATENT DOCUMENTS

| | | | |
|---|---|---|---|
| 10,010,644 B2 * | 7/2018 | Burnett ................. | B01D 53/885 |
| 2012/0080107 A1 | 4/2012 | Kruglick | |
| 2012/0138545 A1 * | 6/2012 | Soler ......................... | C02F 1/30 |
| | | | 422/186.3 |
| 2013/0028796 A1 * | 1/2013 | Nakatani ............ | B01D 53/8603 |
| | | | 422/121 |
| 2021/0128769 A1 * | 5/2021 | Zhang ..................... | A61L 9/014 |
| 2022/0008605 A1 * | 1/2022 | Sood ......................... | A61L 9/20 |

FOREIGN PATENT DOCUMENTS

| | | | | |
|---|---|---|---|---|
| GB | 2515842 A | * | 1/2015 | ............. A61L 9/205 |

OTHER PUBLICATIONS

International Search Report and Written Opinion dated Mar. 18, 2022 in corresponding PCT Application No. PCT/US/2021/055837.

* cited by examiner

*Primary Examiner* — Donald R Spamer
*Assistant Examiner* — Kayla Rose Sarantakos
(74) *Attorney, Agent, or Firm* — Harness, Dickey & Pierce, P.L.C.

(57)     ABSTRACT

A purification system has a reaction chamber, a fan coupled to the reaction chamber communicating air through the reaction chamber, a light source having a first wavelength directed at air passing through the reaction chamber and a surface comprising a photocatalyst. The light source is directed at the surface comprising the photocatalyst.

27 Claims, 15 Drawing Sheets

Air Inlet

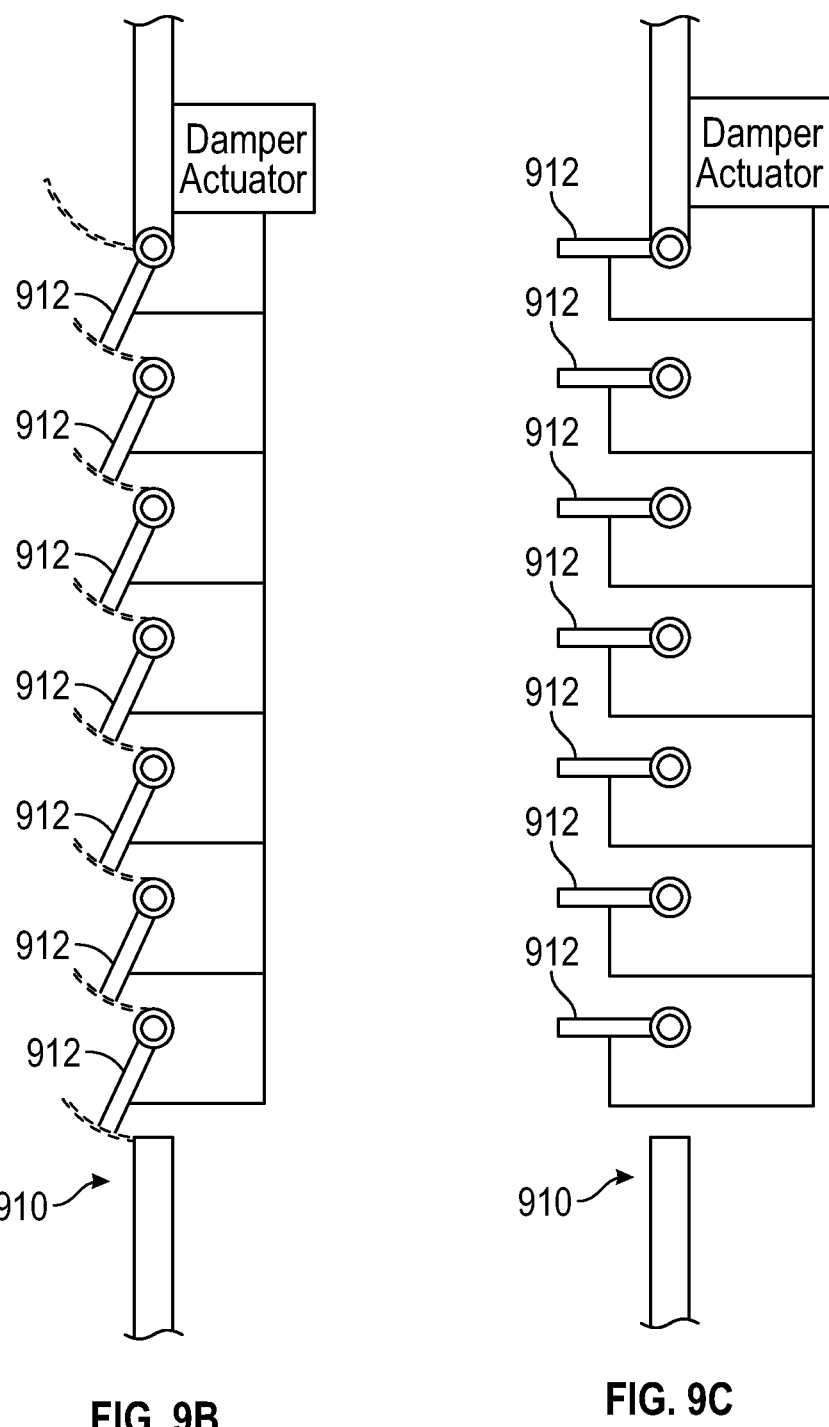
FIG. 9B          FIG. 9C

GERMICIDAL LIGHTING FIXTURE USING PHOTOCATALYTIC OXIDATION

CROSS-REFERENCE TO RELATED APPLICATION

This application is a non-provisional of U.S. Patent Application No. 63/093,859 filed on Oct. 20, 2020. The entire disclosure of the above application is incorporated herein by reference.

TECHNICAL FIELD

The present disclosure relates generally to a germicidal disinfection system and, more specifically, to a system that uses photocatalyst and ultraviolet-C (UVC) light for disinfection.

BACKGROUND

This section provides background information related to the present disclosure which is not necessarily prior art.

Recent outbreaks in respiratory disease and volatile gases in industrial and food service facilities have increased the need for anti-bacterial and anti-viral purification systems that enable cleaner air in living and work spaces for humans. Typical air filters in today's market cannot address the pathogens and viruses that are as small as 100 nm in size. Further, pathogen and viruses may also hide in small fluid droplets that propagate in the air. However, the stand alone air purifiers do address the current issues to a certain extent but they are too localized and costly.

SUMMARY

This section provides a general summary of the disclosure, and is not a comprehensive disclosure of its full scope or all of its features.

The present disclosure provides a system to locally address purification issues such as in a classroom, a meeting room, a manufacturing area or office. Air purification systems set forth herein may be locally place and may be combined with lighting systems.

In one aspect of the disclosure, a purification system has a reaction chamber, a fan coupled to the reaction chamber communicating air through the reaction chamber, a light source a first having a first wavelength directed at air passing through the reaction chamber and a surface comprising a photocatalyst. The light source is directed at the surface comprising the photocatalyst.

In another aspect of the disclosure purification system comprises a reaction chamber comprising an inlet and an outlet. A fan is coupled to the inlet of the reaction chamber communicating air through the reaction chamber to the outlet. A dose control circuit board is coupled to the outlet. The dose control circuit board comprising light sources a first having a first wavelength directed at air passing through the reaction chamber. The dose control circuit board comprises passages therethrough. A surface comprises a photocatalyst. The light sources are directed at the surface comprising the photocatalyst.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected examples and not all possible implementations, and are not intended to limit the scope of the present disclosure.

FIG. 9B is the damper system of FIG. 9A in a partially open position.

FIG. 9C is the damper system of FIG. 9A in a fully open position.

Corresponding reference numerals indicate corresponding parts throughout the several views of the drawings.

DETAILED DESCRIPTION

Figure 1:
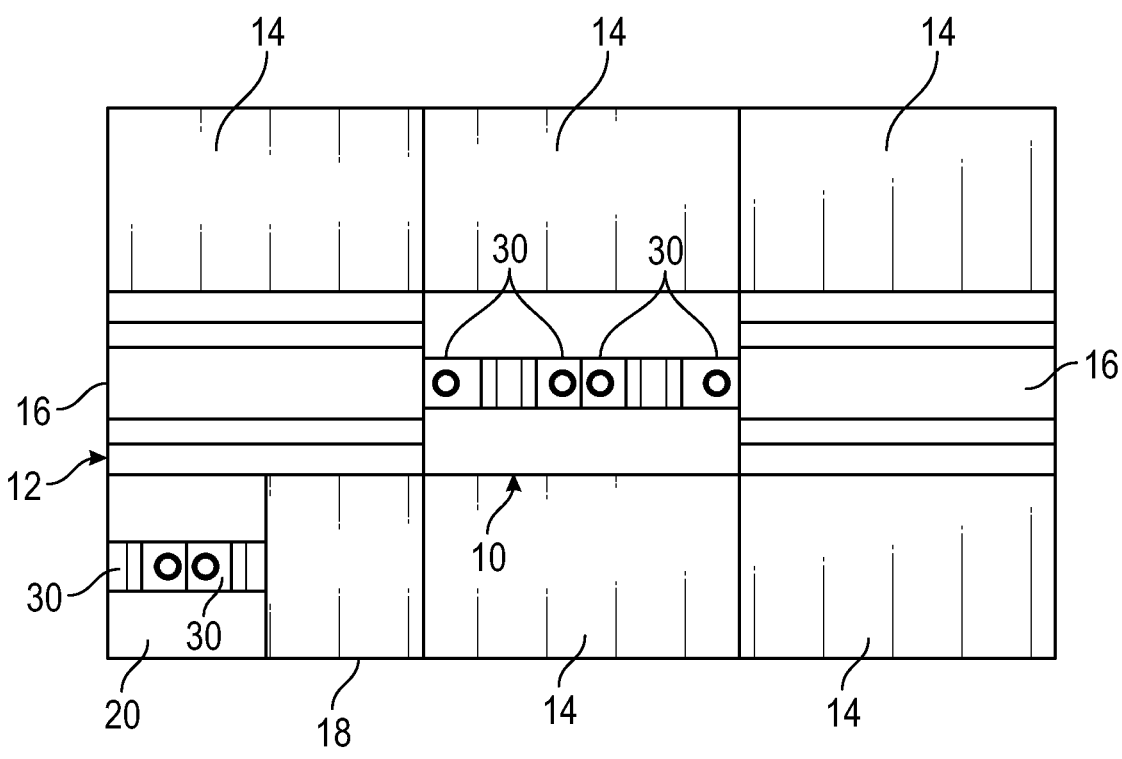
FIG. 1 is a plan view of a ceiling system having purification units according to the present disclosure.

The following description is merely exemplary in nature and is not intended to limit the present disclosure, application, or uses. For purposes of clarity, the same reference numbers will be used in the drawings to identify similar elements. As used herein, the phrase "at least one of A, B, and C" should be construed to mean a logical (A or B or C), using a non-exclusive logical OR. It should be understood that steps within a method may be executed in different order without altering the principles of the present disclosure.

It should be noted that in the following figures various components may be used interchangeably. In the following figures, a lighting assembly is illustrated having various examples that include solid state light sources such as light-emitting diodes (LEDs), organic light-emitting diodes (OLED) and solid state lasers with various wavelengths. Different numbers of light sources and different numbers of wavelengths may be used to form a desired light output and purification depending upon the ultimate use for the light assembly. Visible light in various wavelengths may be generated. Likewise, non-visible wavelengths may be used alone or in combination with the visible wavelengths. UVA, UVB, deep red, and near and far infrared may be used for various environments.

Referring now to FIG. 1, a purification system 10 is illustrated as part of a ceiling system 12, which, in this example, is a suspended ceiling system. The ceiling system 12 may include ceiling tiles 14. In part of this example, the ceiling tiles are 2'×4' suspended ceiling tiles as is commonly found. In addition to the ceiling tiles 14, light fixtures 16 may also be incorporated into the ceiling system 12. The light fixtures 16 may include fluorescent bulbs, incandescent bulbs or light emitting diodes. Light fixtures in a suspended ceiling system may be referred to a troffer. The purification system 10 is incorporated as part of the ceiling system 12 and, in this example, is the same size as the ceiling tiles 14 and the light fixtures 16.

The ceiling system 12 may also include 2'×2' size ceiling tiles 18 and a 2'×2' purification system 20. Each of the purification systems 10, 20 are illustrated as part of the ceiling system 12. However, the purification systems 10, 20 may also be standalone structures mounted at various locations within an enclosed area such as on or recessed within drywall or other structures.

Each of the purification systems 10, 20 includes one or more purification units 30. In the purification system 10, four purification units 30 are illustrated. In the purification system 20, two purification units 30 are provided. Although only one of each of the purification systems 10, 20 are illustrated, various numbers of purification systems may be incorporated into an enclosed area. The room volume and person capacity may be taken into consideration to determine the optimum number of purification units to be installed in any one enclosed area. The purification systems 10, 20 may be used together or only one type may be used in an enclosed area such as a room. Each of the purification units 30 has an air inlet 32 and an air outlet 34. The air inlet 32 draws air from the room below the purification system 10 in a vertical direction. Air exits the purification unit 30 in a direction perpendicular to the direction of the air inlet, in this example, horizontally. That is, air from air outlet 34 generally is directed at in a direction perpendicular to the general direction of the air being received within the air inlet 32. The purification unit 30 may also incorporate light sources 36 thereon. The light sources 36 may be disposed on one or on either side of the purification units 30. The light sources 36 may be LED light sources. Deflectors 38 are disposed on each side of the purification unit may deflect the air and light into the enclosed area such as a room. As described below, the deflectors 38 may be removably coupled to the purification unit 30. The reaction chamber 42, the fan 40 and the light sources 36 are between the two deflectors 38.

Figure 3A:
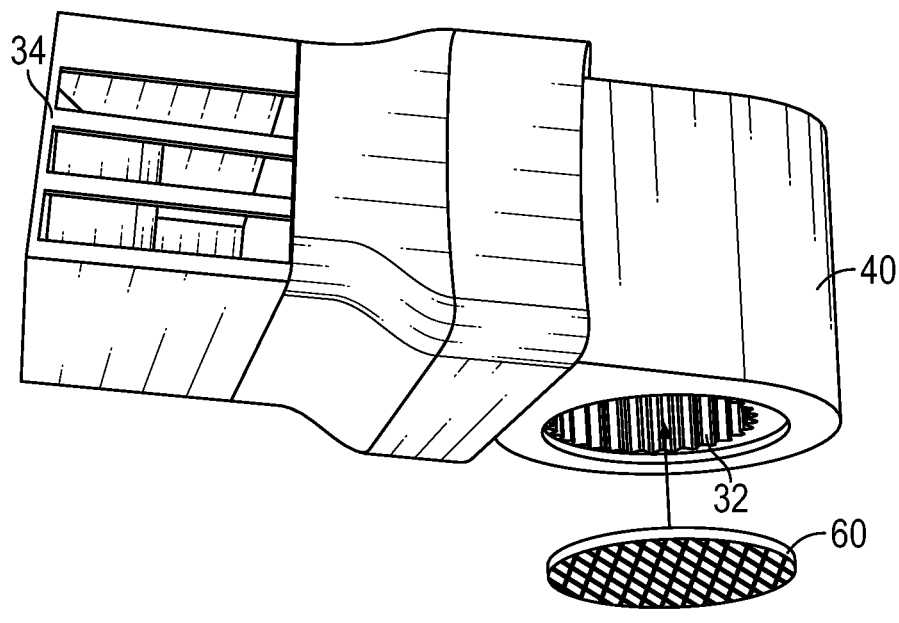
FIG. 3A is a perspective view of a purification unit.
Figure 3B:
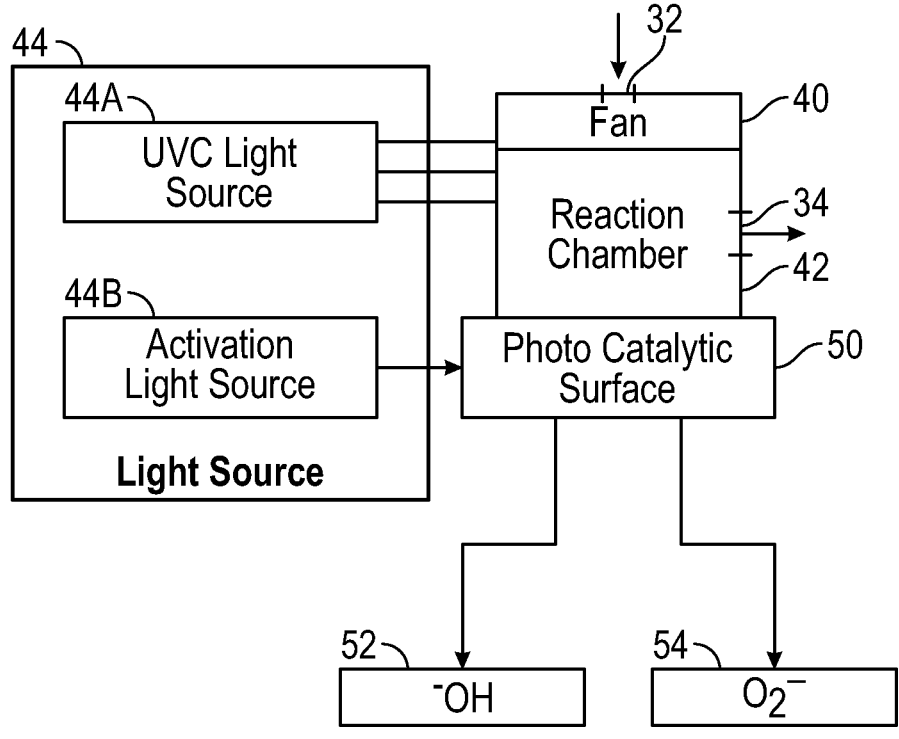
FIG. 3B is a block diagrammatic view of the purification unit.

Referring now to FIGS. 3A and 3B, the purification unit 30 is illustrated in further detail. The purification unit 30 has the air inlet 32 that receives air from the enclosed area. A fan 40 is used to draw air into a reaction chamber 42. The reaction chamber 42 is coupled to a UVC light source 44.

The UVC light source 44 directly irradiates the inlet air and irradiates pathogens therein. The UVC light source 44 generates UVC radiation in wavelengths between 200-280 nm. UVC light or radiation attacks the DNA and RNA structures of pathogens and destroys them. A dose time is the time it takes for the UVC light source 44 to break down DNA and RNA within the reaction chamber 42. Configurations of the reaction chamber 42 to provide an adequate dose time are illustrated below in FIGS. 4A-4E.

As part of the reaction chamber 42 or as part of the deflector 38, a photocatalytic surface or surfaces 50 may be incorporated into the system. The photocatalytic surface 50 and the position thereof within the reaction chamber 42 is described below. The photocatalytic surface 50 may use an activation light source 44B. The activation light source 44B may include the UVC spectrum but may also be broader that the UVC spectrum such as less than 387 nm.

The photocatalytic surface 50 may be composed of titanium dioxide ($TiO_2$). When titanium dioxide is irradiated with light of 387 nm or shorter in the presence of humidity, hydroxyl groups 52 (—OH) and super oxygen groups 54 ($O_2'$) are formed. Both hydroxyl groups and super oxygen groups kill airborne pathogens. A coating on the deflector 38 or coating on the walls used within the reaction chamber 42 may be combined with zinc oxide (ZnO) nanoparticles to form the photocatalytic surface 50. That is, nanoparticles of titanium dioxide and zinc oxide may be used within the reaction chamber 42 and the deflector 38 as the photocatalytic surface 50.

A filter 60 may also be incorporated over the inlet 32. The filter 60 may be used to filter large particles from entering the air inlet 32. The filter 60 may also be provided to make the purification units 30 more aesthetically pleasing with a suitable style.

As is best illustrated in FIG. 3A, the discharge from the air outlet 34 may have an increased velocity compared to the inlet air provided to the reaction chamber 42 by the fan 40. By reducing the area of the air outlet 34, a nozzle effect increases the velocity while providing a longer dwell time of the air to become irradiated within the reaction chamber 42. The dosage of the air within the system is the watts divided by the area multiplied by the time within the reaction chamber 42. That is, as the time within the reaction chamber 42 increases, the dosage also increases and therefore, the reducing of pathogens is increased.

Figure 2A:
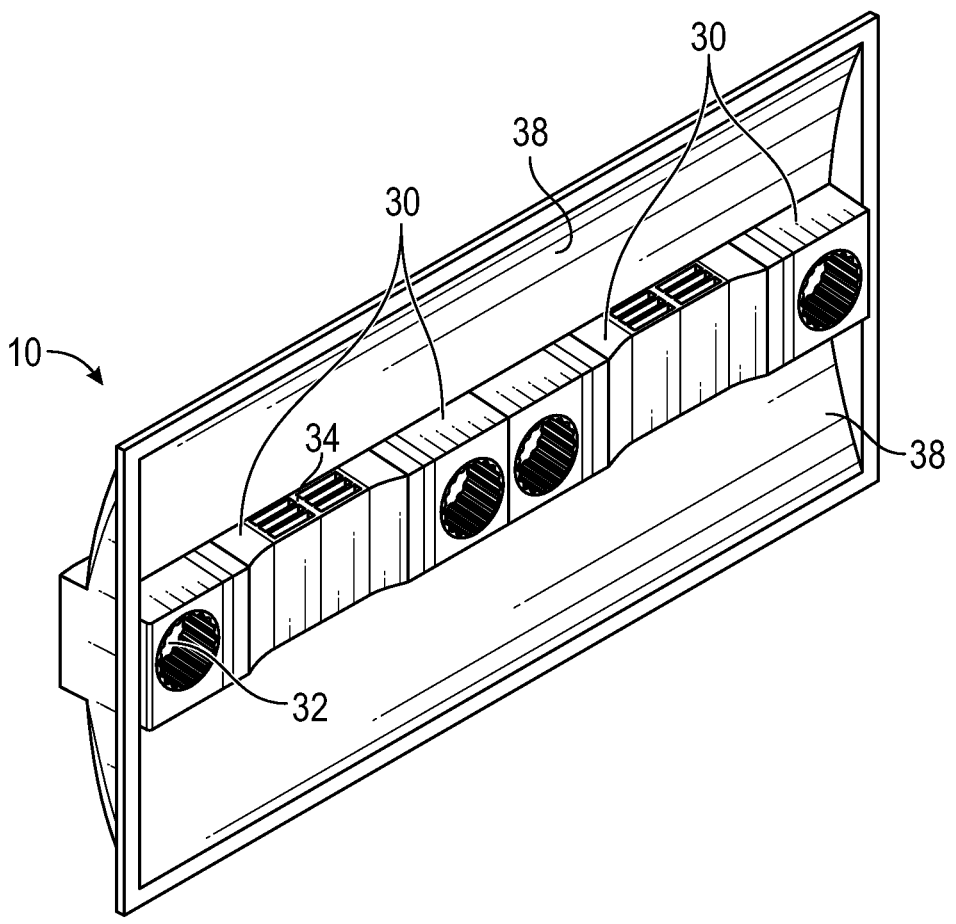
FIG. 2A is a perspective view of a purification system.
Figure 2B:
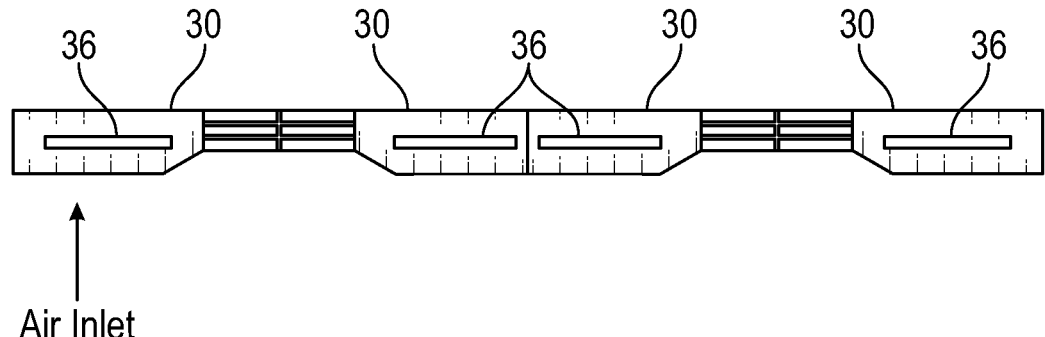
FIG. 2B is a side view of the purification units of a purification system.
Figure 2C:
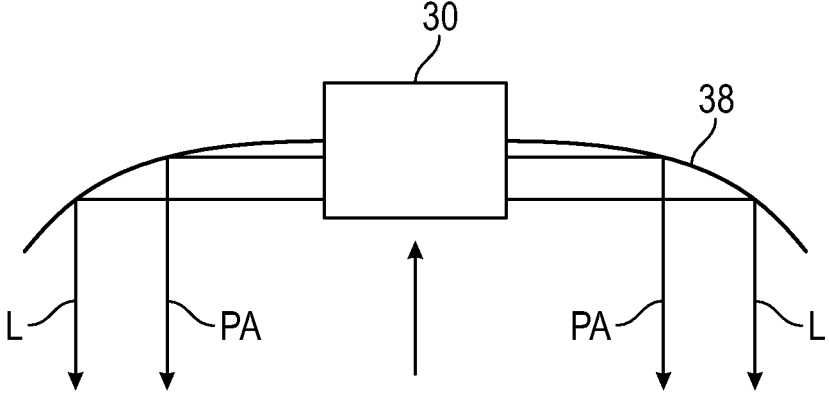
FIG. 2C is a side view of light rays and air flow at a purification system.

Referring now to FIG. 2C, a side view of the system of FIG. 2A is set forth. The purification unit 30 is shown relative to the deflector 38. Both light L and purified air PA are deflected by the system should the system include light sources 36. When the light sources 36 are not included on the outside of the purification units 30, no light L is deflected by the deflectors 38. When light L is not be deflected by the deflectors 38, the deflectors may not have a titanium dioxide or zinc oxide coating disposed thereon.

Figure 4A:
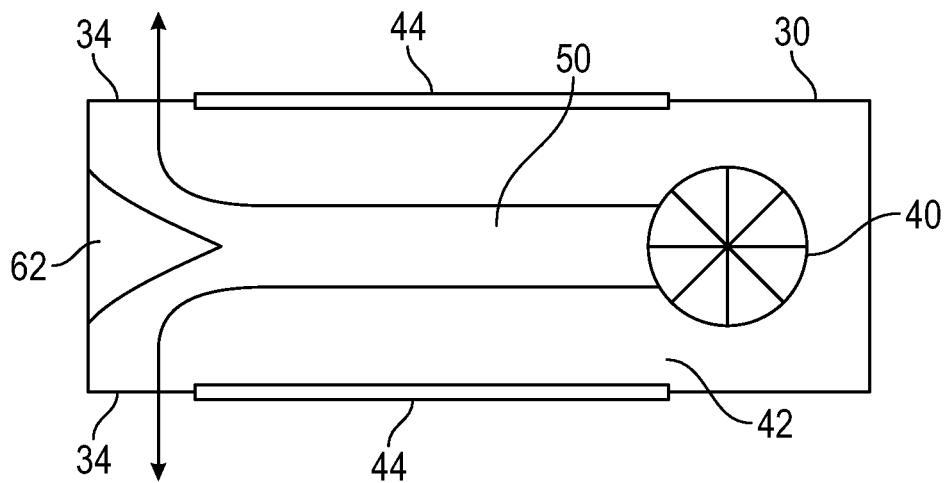
FIG. 4A is a cutaway view of one example of a purification unit.

Referring now to FIG. 4A, a first example of a purification unit 30 is set forth. In this example, the fan 40 is illustrated communicating air through the reaction chamber 42. A diffuser 62 deflects the air out of the air outlets 34. The light source 44 may provide wavelengths that were described above relative to the UVC light source 44A and the activation light source 44B. However, the light source 44 may only provide UVC light depending upon the configuration. The speed of the air from the fan may be adjusted to obtain a desired dose. The interior of the reaction chamber 42 may be comprises of photocatalytic surfaces 50.

Figure 4B:
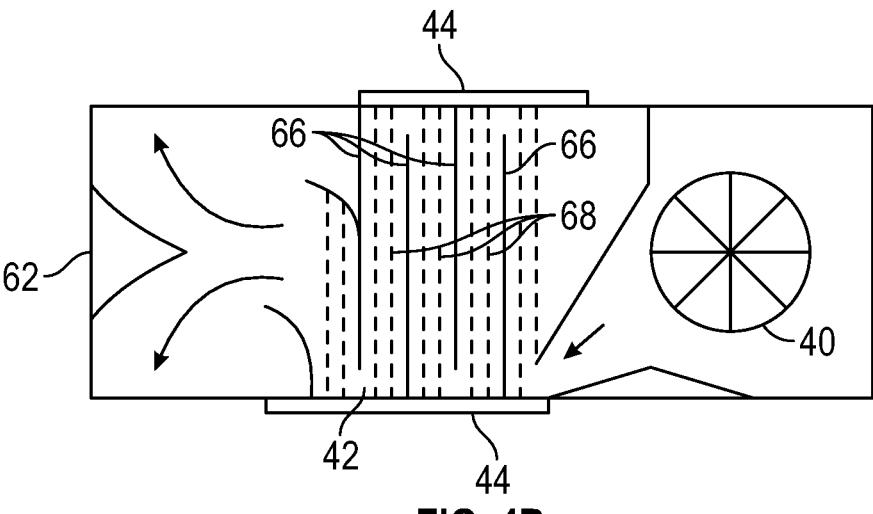
FIG. 4B is a cutaway view of a second example of a purification unit.

Referring now to FIG. 4B, baffles 66 are incorporated into the reaction chamber 42. The reaction chamber 42 thus provides a longer path to the air discharged from the fan 40. That is, a longer dwell time for the air within the reaction chamber 42 is provided. The light sources 44 direct light through flow cavities 68 defined by the baffles 66. The cavities extend laterally across the reaction chamber 42. Openings from the baffles 66 are alternated on each side of the cavities 68 to increase the path of the air travelled. In FIGS. 4A and 4B, light sources may be provided on two opposing sides of the reaction chamber 42. However, light sources 44 may be incorporated on each wall of the reaction chamber 42.

Figure 4C:
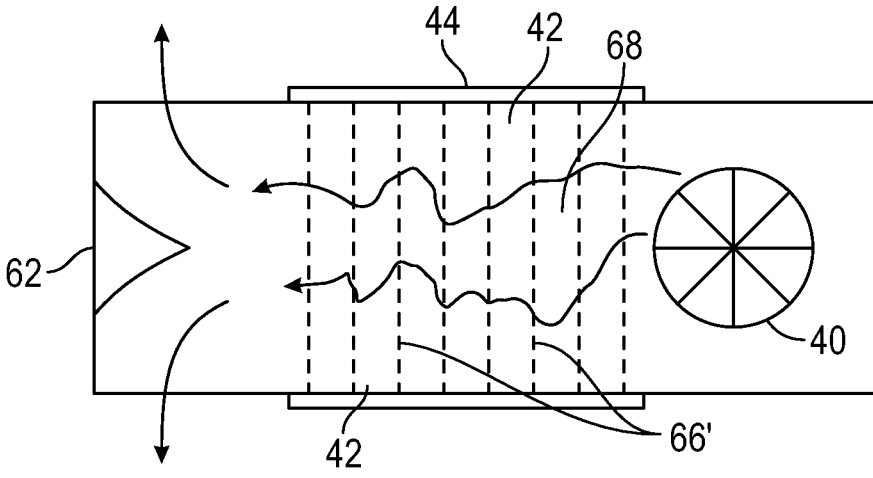
FIG. 4C is a cutaway view of a third example of a purification unit.

Referring now to FIG. 4C, the baffles 66 are altered with multiple openings 66'. The openings may be randomly spaced so that a longer path of the air discharged from the fan is provided through the reaction chamber 42. The openings 66' may be at various spacing and various heights to provide the longer air path. The proper dwell time may be experimentally determined based upon the air flow from the fan 40, the pathogens desired to be eliminated and the size of the reaction chamber 42.

Figure 4D:
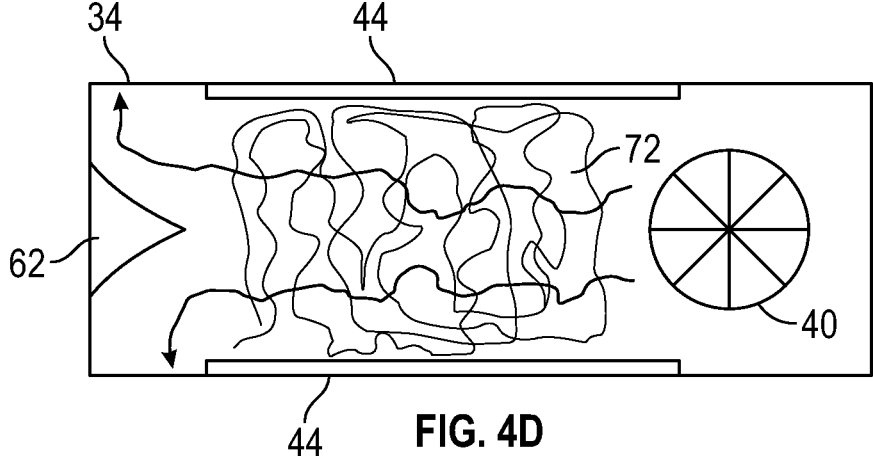
FIG. 4D is a cutaway view of a fourth example of a purification unit.

Referring now to FIG. 4D, a mesh material 72 may be provided between the fan 40 and the outlet 34. The mesh material 72 provides a longer path within the reaction chamber 42 and thus an increase in the dosage.

Figure 4E:
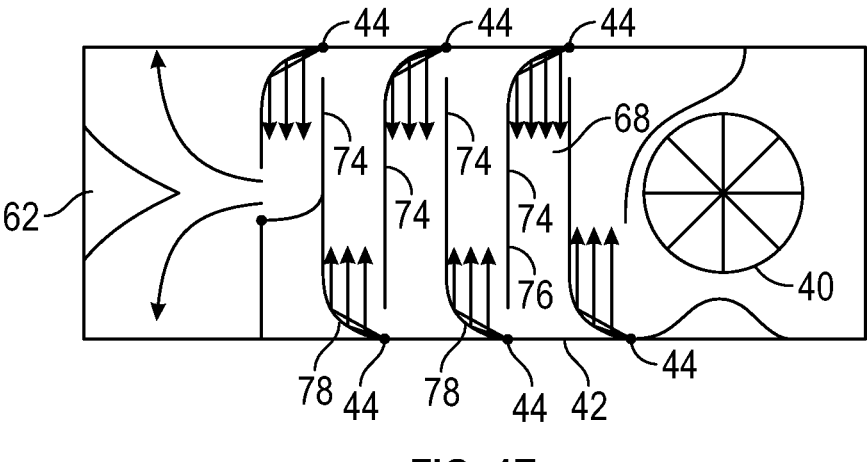
FIG. 4E is a cutaway view of a fifth example of a purification unit.

Referring now to FIG. 4E, the reaction chamber 42 includes a shaped baffle 74. The shaped baffle 74 includes a straight portion 76 that is similar to that illustrated in FIG. 4B. However, the baffle 76 includes a curved portion 78. The curved portions 78 of the shaped baffles 74 may be parabolic in shape. The curved portions 78 may be a portion of a parabolic cylinder. The light source 44 may be individually dispersed at the intersection of the curved portion 78 and the housing of the reaction chamber 42. Light incidence upon the curved portion 78 is directed in parallel down the cavities 68. The curved portion 78 may have a dimension as wide as the cavity 68 so that light travels between two adjacent baffles and fills the cavity 68. The light from the light sources may extend vertically and correspond directly to the shape of the curved portions 78 of the shaped baffles 74.

Figure 5:
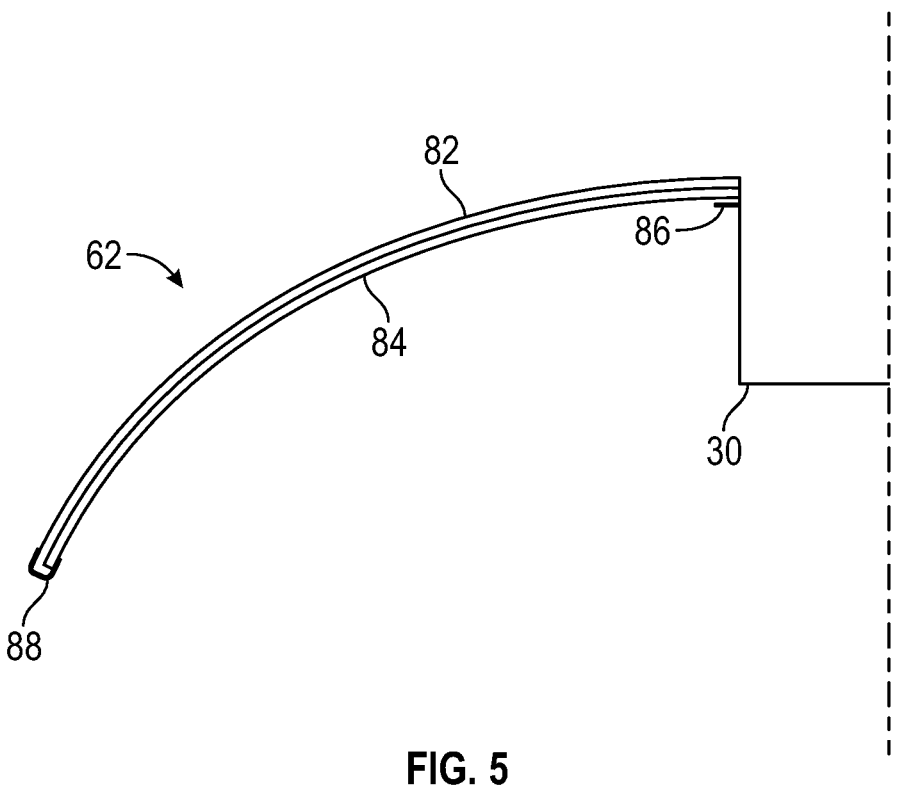
FIG. 5 is a side view of a replaceable structure for a purification system.

Referring now to FIG. 5, one example of a diffuser 62 is set forth relative to the purification unit 30. The diffuser 62 may have a structure 82 that is rigid. The structure 82 is directly adjacent to a flexible diffuser surface 84. The flexible diffuser surface 84 may be replaceable. That is, the flexible diffuser surface 84 may include both zinc oxide and titanium dioxide nanoparticles thereon. After a while, the titanium dioxide and zinc oxide nanoparticles may be less effective. In this manner, the flexible diffuser surface 84 may be removed and replaced. Flexible diffuser surface 84 may engage in a groove 86 adjacent to the purification unit 30. A fastener 88 may couple and retain the flexible diffuser surface 84 into the groove 86 so that the surface 84 conforms to the structure 82. The fastener 88 may be a clip, threaded fastener, adhesive or the like. Preferably, the fastener 88 is removable to allow the flexible diffuser surface 82 to be quickly and easily replaced.

Figure 6A:
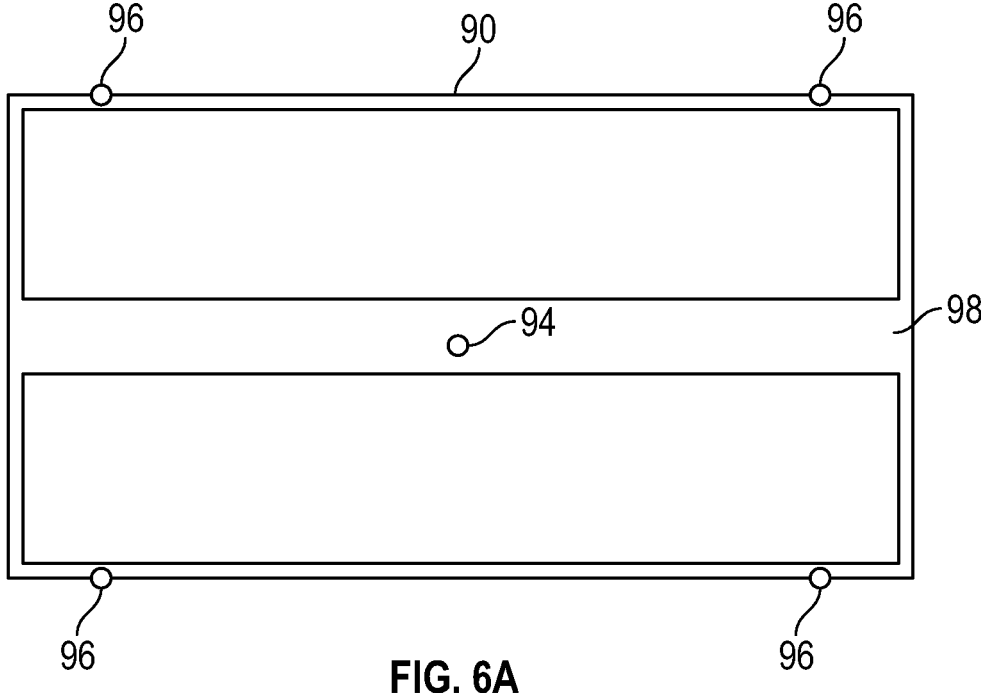
FIG. 6A is a frame structure for a purification system.
Figure 6B:
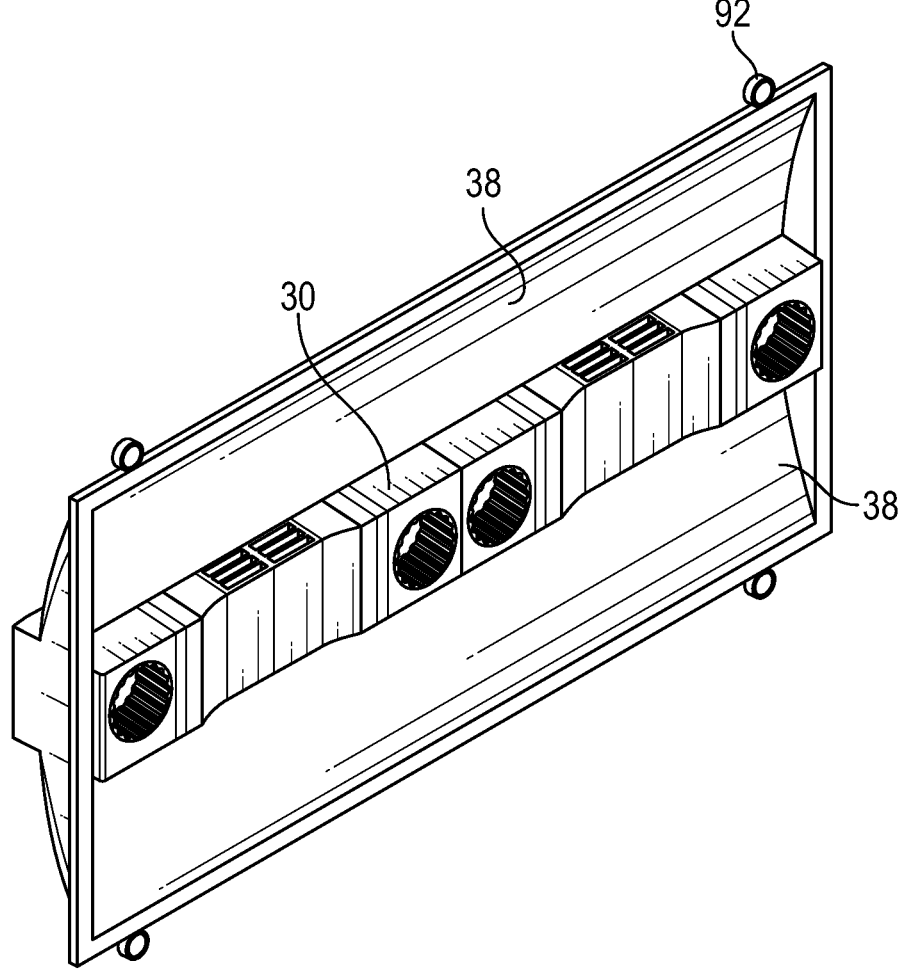
FIG. 6B is the replaceable structure for a purification system that is coupled to the frame of FIG. 6A.

Referring now to FIGS. 6A and 6B, the purification system 10 may also include a frame structure 90 that is intended to be permanently mounted to the ceiling system 12. The frame structure 90 may be formed of stamped metal and is curved to accommodate the shape of the diffuser and purification unit assembly illustrated in FIG. 6B. That is, a replaceable structure 92 including both the deflector 38 and the purification units 30 may be provided. The replacement structure 92 may be formed entirely of plastic and may be powered through a power opening 94. A plug or other type of connector may be incorporated within the power opening 94 to power the replaceable structure 92. The replaceable structure 92 may last for many years, such as up to five years. The purification units 30 may be integrally formed in the replaceable structure with the fans 40 preinstalled so that an installer my install a single unit quickly and easily. The replaceable structure 92 may be rigid enough to allow fasteners 96 to removably fasten the entire replaceable structure 92 to the frame structure 90. Of course, the frame structure 90 may include a cross member 98 onto which further fasteners may be provided. The cross member 98 has the power opening 94 therein.

Figure 7A:
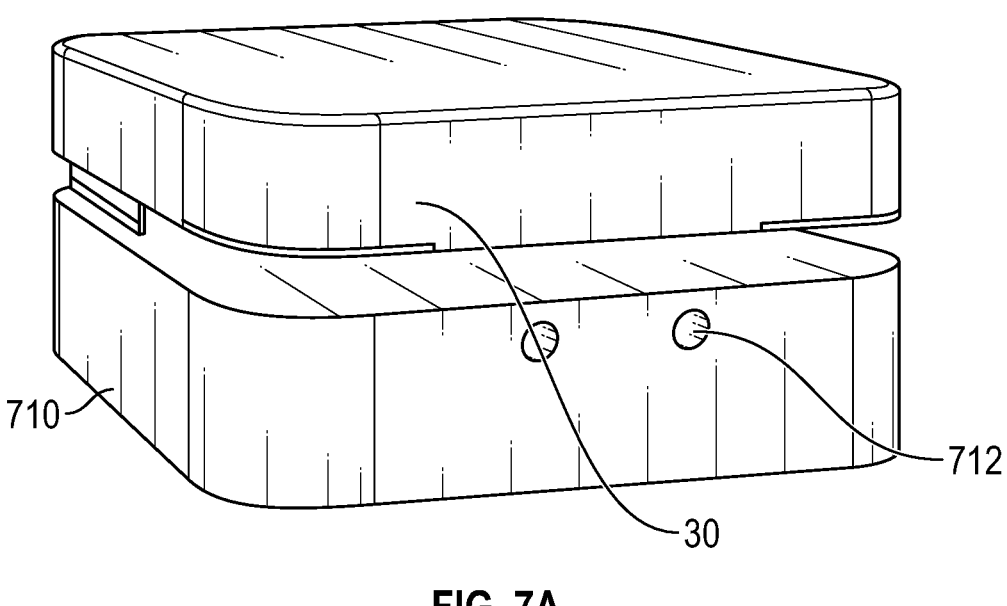
FIG. 7A is an autonomous mobile platform with a purification system therein.

Referring now to FIG. 7A, a purification unit 30 may also be incorporated into a mobile platform 710. The mobile platform 710 may have sensors 712 to allow the system to autonomously move through an enclosed area such as a building.

Figure 7B:
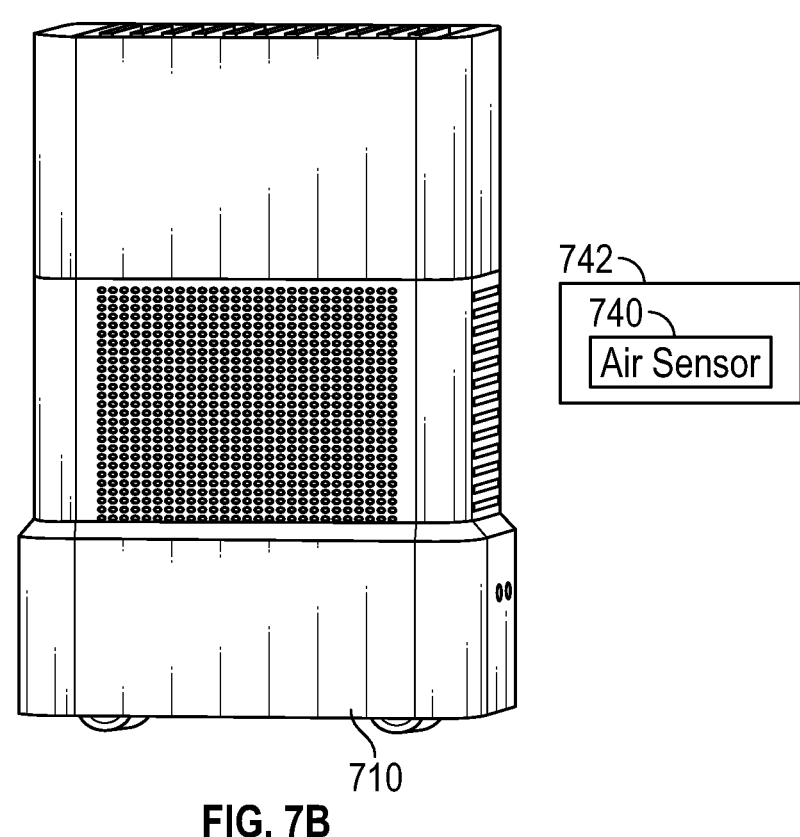
FIG. 7B is a second example of an autonomous mobile platform having an air purification system therein.
Figure 7C:
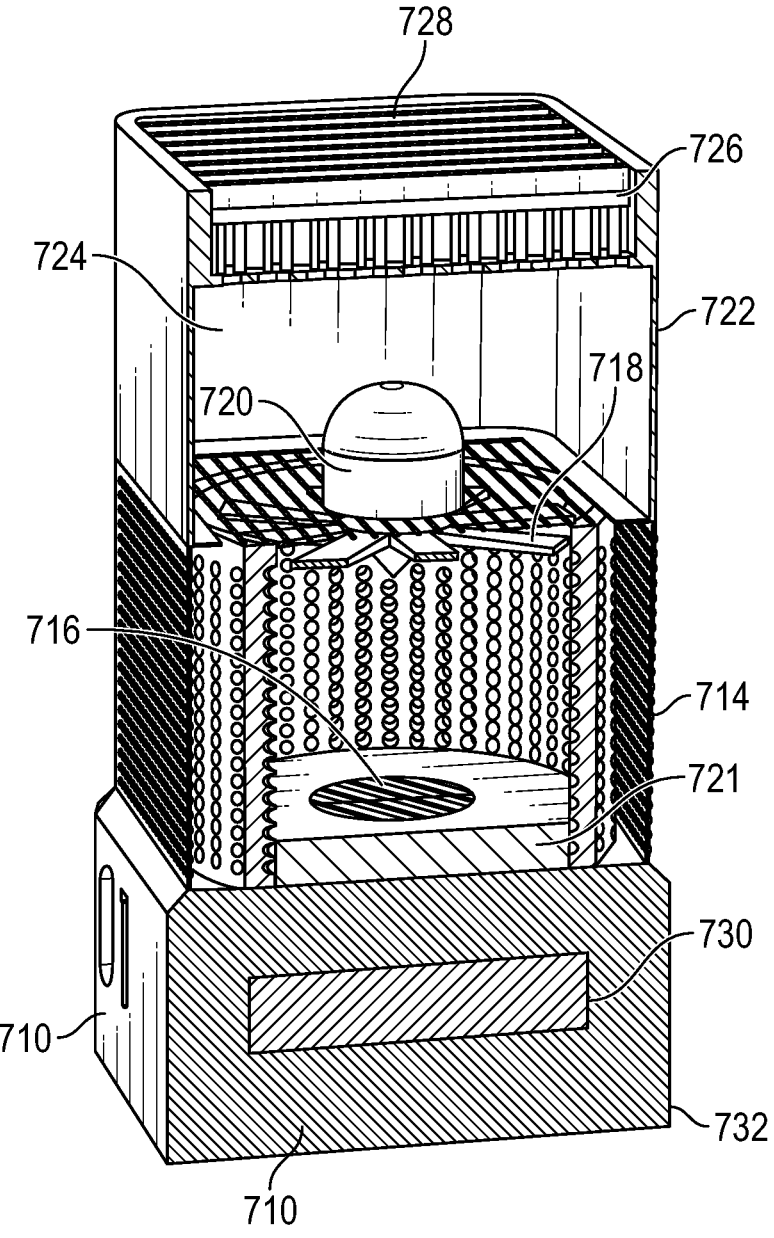
FIG. 7C is a cutaway view of an autonomous mobile platform of FIG. 7B.

Referring now to FIGS. 7B and 7C, the mobile platform 710 is illustrated in further detail. The mobile platform 710 has an inlet 714 that has a mesh 716 that may act as a filter. A fan draws air into the inlet 714 in much the same manner as that described above. A light source 720 that may be coupled to the fan 718 generates light in the appropriate wavelength, such as the UVC wavelength or wavelengths just greater than the UVC wavelength through the UVC spectrum. A humidifier 721 may also be coupled adjacent to the inlet 714 to humidify the air and assist in the photocatalytic reaction. A photocatalytic surface 722 may be incorporated into a reaction chamber 724. A filter 726 may be placed adjacent to an air outlet 728 to provide resistance to the air flow through the reaction chamber 724 to allow an increased dwell time therethrough. The photocatalytic surface 722 and the light from the light source 720 act in the same manner described above in FIGS. 1-6. In this manner, the autonomous mobile platform control electronics 730 may be located within a base 732 of the autonomous mobile platform 710. The sensors 712 may also sense the amount of impurities in the air and thus direct the autonomous unit to a particular location. The system may also be directed by an external source such as the air handling system of the building. That is, air sensor 740 may communicate signals to the control electronics 730 based upon impurities or pathogens within the air handling system 742 of the building. Certain areas or volumes within the building may have higher levels of pathogens therein which are detected by the air sensors 740. The autonomous vehicle 710 may thus be dispatched to the pathogen location.

Figure 8A:
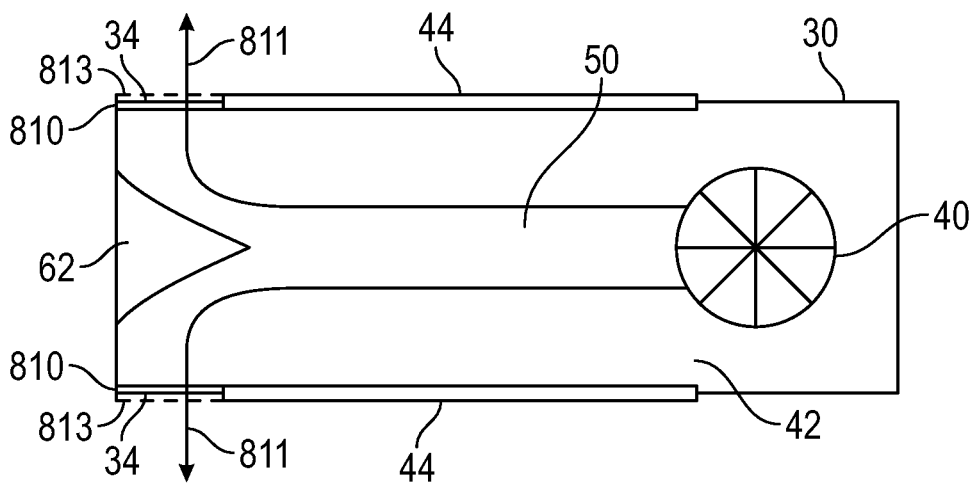
FIG. 8A is a cutaway view of a purification unit having a dose control circuit board at the outlet.

Referring now to FIG. 8A, an example similar to that set forth in FIG. 4A is set forth. In this example, the same reference numerals are used to identify the same components. A dose control circuit board 810 is placed at the air outlet 34. In this example, the light sources 44 are optional. The dose control circuit board 810 has a passage or passages therethrough to allow the air that has been purified from within the reaction chamber 42 to escape. As will be described in more detail, the speed of the fan 40 may be controlled to vary the amount of air flowing through the passages of the circuit board 810 and therefore control the dosage to the air that is to be purified within the reaction chamber 42. A filter 813 may also be disposed at the outlet 34 to create back pressure into the reaction chamber 42. The filter 813 may be placed before or after the circuit board 813 in terms of airflow out of the reaction chamber 42. The filter 813 may be a HEPA filter. The filer 813 may be easily replaceable during regular maintenance.

Figure 8B:
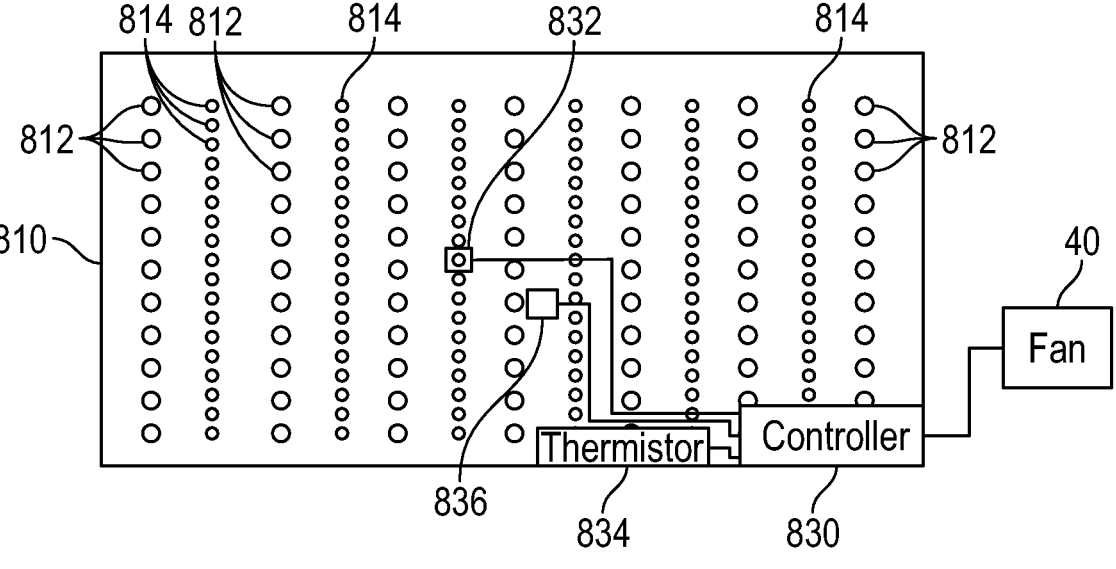
FIG. 8B is a plan view of a first example of the dose control circuit board viewed from within the reaction chamber.

Referring now to FIG. 8B, one example of a dose control circuit board 810 is set forth. In this example, LEDs 812 are disposed throughout the circuit board 810. The LEDs 812 may be UVC LEDs. In this example, the LEDs 812 are placed in vertical rows. However, various arrangements and spacings of LEDs 812 may be used. The number of LEDs 812 may vary depending on the size of the reaction chamber 42 and the dose desired. The LEDs 812 are directed at the incoming flow of air at the circuit board 810. The circuit board 810 also has thermal vias 814 disposed thereon. The thermal visas 814 are illustrated in vertical rows between two rows of LEDs 812. However, the spacing and position of the thermal vias 814 may be varied. The thermals vias 814 are air passages that extend through the circuit board 810. Thus, the thermal vias 814 allow air that is within the reaction chamber 42 to pass therethrough while being treated with UVC light from the LEDs 812.

The amount of air within the reaction chamber 42 may be controlled by a controller 830. The controller 830 may be coupled to various sensors such as a flow sensor 832, a temperature sensor such as a thermistor 834 and a pressure sensor 836. Ultimately, the controller controls the speed of the fan 40 based on the one or more sensor signals from the one or more sensors.

The controller 830 may be microprocessor-based and programmed to perform various steps described below. The controller 830 receives a flow signal, such as flow rate signal, from the flow sensor 832. The flow signal corresponds to an amount of flow through the circuit board 810. The controller 830 receives a temperature signal from the thermistor 834. The temperature signal corresponds to the temperature at the circuit board which corresponds to the temperature of air within the reaction chamber. The pressure sensor 836 generates a pressure signal corresponding to the pressure within the reaction chamber 42. Operation of the circuit board 810 is described below.

Figure 8C:
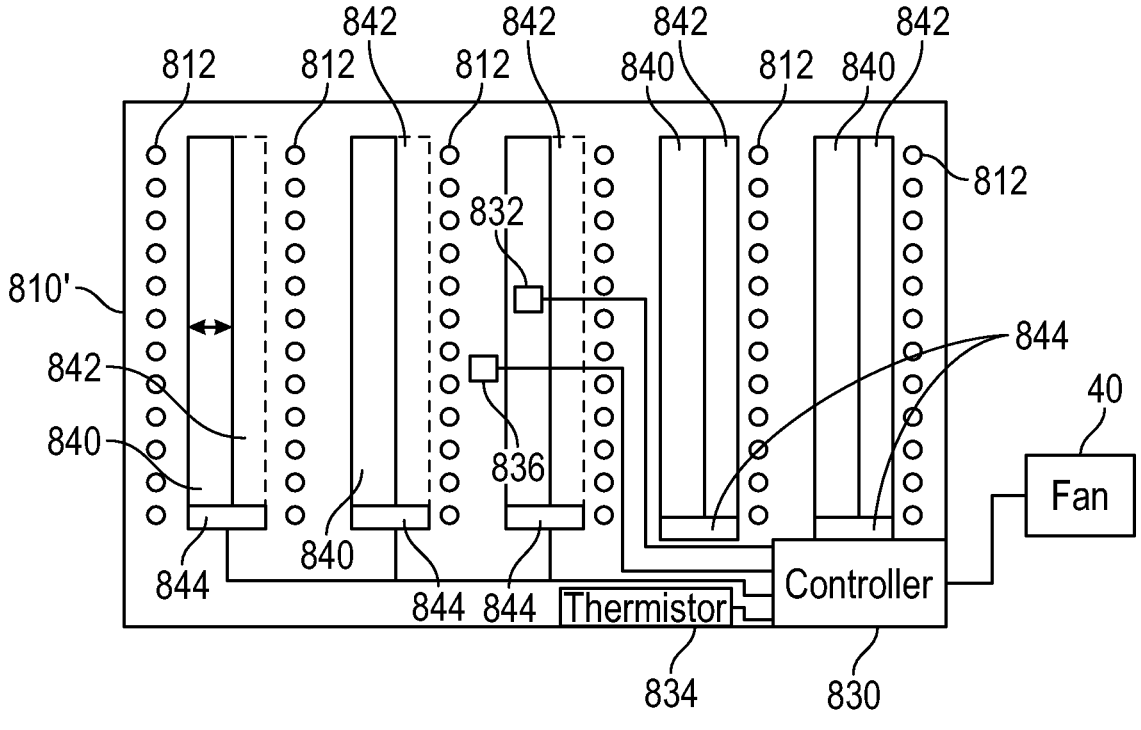
FIG. 8C is a plan view of a second example of a dose control circuit board when viewed from the reaction chamber.

Referring now to FIG. 8C, an alternate example of a dose control circuit board 810' is set forth. The dose control circuit board 810' includes the controller 830, the flow sensor 832, the thermistor 834 and the pressure sensor 836. In addition, rows of LEDs 812 are also illustrated. In this example, the thermal vias 814 have been replaced by openings 840 that have a door 842 that is controlled by an actuator 844.

In operation of FIGS. 8A-8C, the controller 830 may use feedback or one or more of the sensors 832-836 to control the speed of the fan 40 so that the air within the reaction chamber 42 has the desired amount of dose of UVC light. The speed of the fan 40 can thus be variable from on to off or anywhere therebetween. By slowing the flow through the reaction chamber 42 the dose (the amount of light incident upon the air within the reaction chamber 42 is increased). The LEDs 812 increase the temperature within the reaction chamber. The elevated temperature within the reaction chamber 42 helps eliminate pathogens within the air of the reaction chamber 42. The LEDs 812 are directed directly opposite the air flow as is best illustrated by the arrows 811 in FIG. 8A. Thus, the air flow that reaches the circuit board 810 is further illuminated by the UVC LEDs 812. This allows more pathogens to be eliminated and destroyed before the treated air leaves through the thermal vias 814 of FIG. 8A or through the openings 840 in FIG. 8B.

The controller 830 may purely rely on the flow rate as measured by the flow sensor 832. The speed of the fan 40 can be changed to increase or decrease the flow through the circuit board 810 to allow the air to dwell within the reaction chamber longer and thus provide a greater reduction in pathogens.

The controller 830 may also use the thermistor 834 and the temperature signal from the thermistor 834 to control the speed of the fan 40. As the reaction chamber 42 heats, a high temperature may be maintained and thus the fan speed reduced to keep the reaction chamber 42 at a certain temperature for a certain amount of time. When the temperature and time limits have been reached, the speed of the fan 40 may be increased to push the air from the reaction chamber into the room. The flow signal can be used in combination with the temperature signal so that the fan speed is set to provide a desired flow rate.

The pressure sensor 836 may also be used to control the fan speed of the fan 40. That is, a pressure signal generated from the pressure sensor 836 may be communicated to the controller 830 to control the speed of the fan 40. That is, a lower pressure allows the air within the reaction chamber 42 to dwell longer. After a predetermined amount of time measured by the controller 830, the air within the reaction chamber 42 may have a sufficient dosage and thus be evacuated from the reaction chamber by increasing the speed of the fan 40.

The door 842 may also be controlled in a similar manner. By controlling the opening size of the door 842, the amount of flow of air through the reaction chamber 42 and thus the dose may be controlled. In a similar manner to that described above, the door 842 may be opened to allow the purified air to leave the reaction chamber 42. When a higher dosage is required, the door 842 may be closed or partially closed to restrict the airflow from the reaction chamber 42. The flow signal from the flow sensor 832 may allow the controller 830 to determine the dose and thus control the fan speed. Likewise, the thermistor 834 may provide an indication of the temperature within the reaction chamber 42 to allow the controller 830 to control the speed of the fan. As mentioned above, when the temperature within the reaction chamber 42 is elevated for a certain amount of time, a proper dose may be achieved. Likewise, the pressure sensor 836 generates a pressure signal to allow the dosage to be controlled and the controller 830 to control the speed of the fan in response to the pressure signal. In both examples, in FIGS. 8B and 8C, one or more of the sensors may be used in controlling the dosage of the air within the reaction chamber.

Figure 9A:
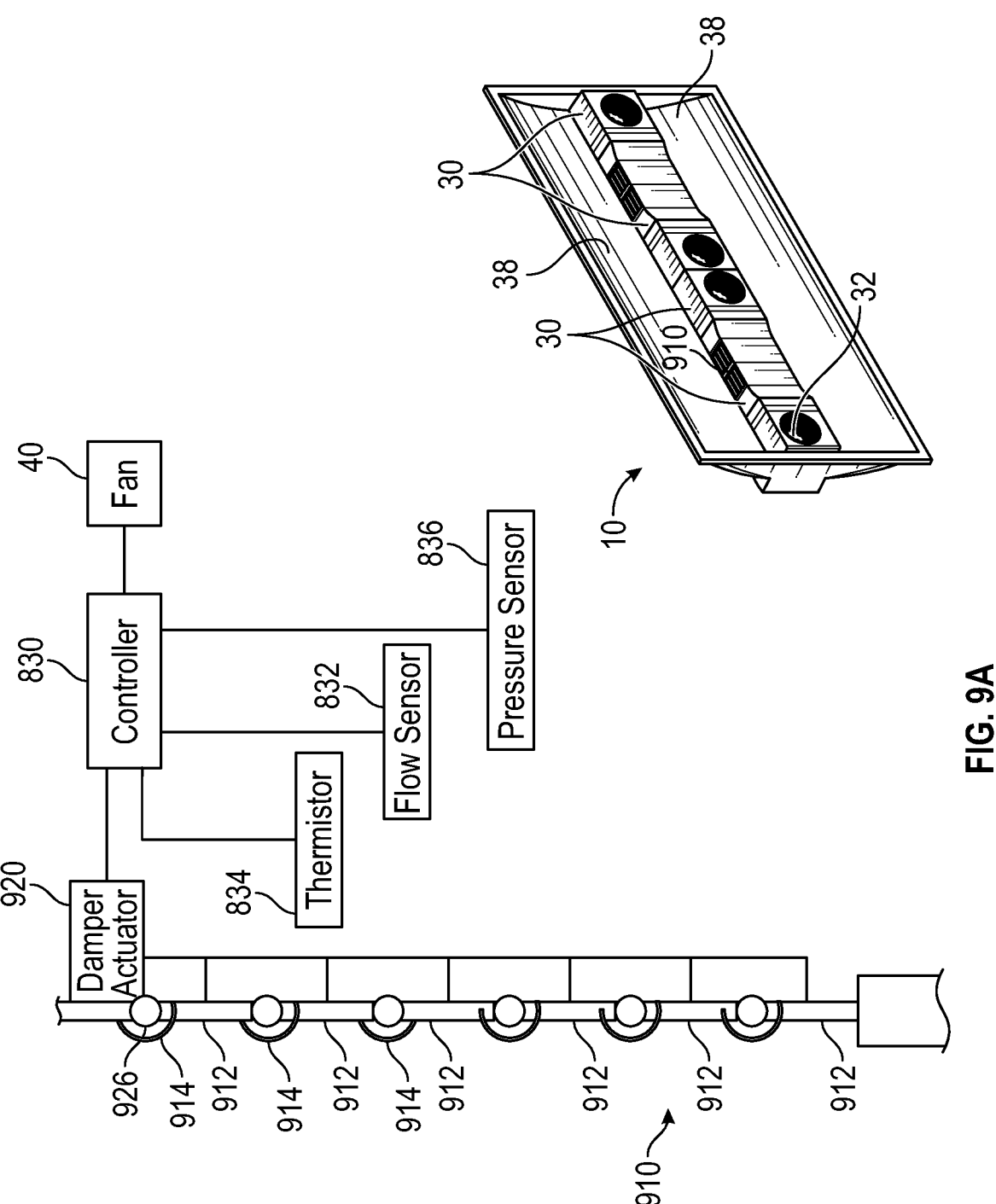
FIG. 9A is a damper system for the outlet.

Referring now to FIGS. 9A-9D, the air outlet 34 may have a damper 910 coupled thereto. The damper 910 may be a controllable damper that allows the amount of air within the reaction chamber 42 to be controlled. That is, the flow of air through the reaction chamber 42 may be controlled by the opening and closing of the damper 910. The damper 910 may include one or more damper doors 912. The damper doors 912, in this example, are aligned linearly when closed as illustrated in FIG. 9B. In this example, six damper doors 912 are illustrated. However, various numbers of damper doors including one or more may be provided. The damper doors 912, in this example, rotate between a closed position as illustrated in FIG. 9A, a partially open position, as illustrated in FIG. 9B, and a completely open position in FIG. 9C. The doors 912 may also be sliding doors or other types of variable opening orifices.

As illustrated in FIGS. 9A-9C, springs 914 may be coupled to the doors 912. The springs 914 may provide a resistance to opening and thus allow a certain pressure to build within the reaction chamber 42 to allow a dosage to be achieved. That is, until a certain pressure builds within the reaction chamber 42, the damper doors 912 remain closed allowing a certain dosage. When a higher pressure is reached, the spring opens. The higher pressure may be achieved by increasing the speed of the fan 40

Figure 9D:
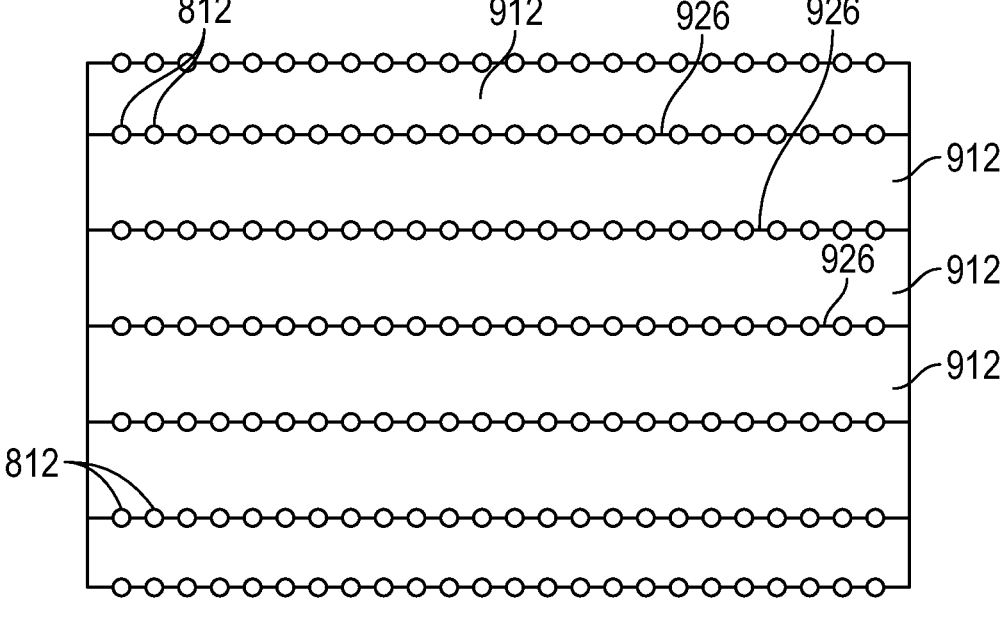
FIG. 9D is a plan view of the rear side of the damper system of FIG. 9A illustrating the light sources therein.

A damper actuator 920 may be used to control the opening and closing of the damper doors 912. The controller 830, the flow sensor 832, the thermistor 834 and the pressure sensor 836 from FIGS. 9A and 9B may be used in a similar manner to that described above. That is, the control of the damper doors 912 may be performed in a similar manner to that described above relative to FIG. 9C. As is best illustrated in FIG. 9D, a plan view from the inside of the reaction chamber 42 of the damper doors 912 is set forth. In this example, a structure adjacent to the doors 912 such as the door mounts 926 may have the LEDs 812 coupled thereto. The LEDs 812 remain fixed and continually direct light toward the oncoming air while the damper doors 912 rotate to an open position. The LEDs 812 face the air being exhausted through the doors 912 and thus eradicate the pathogens in the reaction chamber 42.

The damper actuator 920 may be an arm, a piezoelectric device, a molar or the like. The damper actuator 920 moves the damper doors 912 in response to control signals from the controller 830. As mentioned above, one or more of the sensors 832, 834, 836 may communicate signals to the controller 830. Based on the signals from the one or more sensors 832, 834, 836, the opening and closing of the damper doors 912 by way of the damper actuator 920 is controlled by the controller 830. The doors 912 provide resistance to the flow of air through the reaction chamber 42 that can be varied when closed or partially closed. The fan speed of the fan 40 may also be controlled in a similar manner using the signals from the sensors 832, 834 and 836. To allow a longer dose, the damper doors 912 may be partially or fully closed and the fan speed may be low. To exhaust the air within the reaction chamber 42 after a proper dose has been achieved, the damper doors 912 may be opened and the fan 40 increased in speed. The controlling relative to the temperature, pressure and flow operates in the same way as that described relative to FIG. 8C.

The foregoing description of the examples has been provided for purposes of illustration and description. It is not intended to be exhaustive or to limit the invention. Individual elements or features of a particular example are generally not limited to that particular example, but, where applicable, are interchangeable and can be used in a selected example, even if not specifically shown or described. The same may also be varied in many ways. Such variations are not to be regarded as a departure from the invention, and all such modifications are intended to be included within the scope of the invention.

What is claimed is:

1. A purification system for a ceiling system comprising:
a housing having a lateral direction and a longitudinal direction;
a first deflector;
a plurality of baffles each comprising a parabolic portion having a curved surface with a photocatalyst;
a reaction chamber comprising a plurality of flow cavities extending across the reaction chamber in the lateral direction defined by the plurality of baffles disposed within the reaction chamber;
a fan coupled to the reaction chamber communicating air into the reaction chamber and the flow cavities therein; and
a plurality of light sources, each light source associated with a respective one of the plurality of baffles so that each light source is positioned in each flow cavity at an intersection of the respective baffle and the housing, each light source having a first wavelength and each light source generating light directed at the surface of the parabolic portion having the photocatalyst so that light reflected from the parabolic portion is directed in a parallel direction within the flow cavities and laterally within the flow cavities and at air passing laterally through the flow cavities in a direction of the air within the flow cavities.

2. The purification system of claim 1 wherein the fan directs air from within the reaction chamber to the curved surface of each of the plurality of baffles.

3. The purification system of claim 1 wherein the light source comprises a first light source generating light at a first wavelength and a second light source generating light at a second wavelength.

4. The purification system of claim 3 wherein the first wavelength comprises a first plurality of wavelengths from 200 nm to 280 nm.

5. The purification system of claim 4 wherein the second wavelength comprises a second plurality of wavelengths at or below 500 nm.

6. The purification system of claim 4 wherein the second wavelength comprises a second plurality of wavelengths at or below 387 nm.

7. The purification system of claim 1 wherein the photocatalyst comprises titanium dioxide.

8. The purification system of claim 1 wherein the photocatalyst comprises titanium dioxide and zinc oxide.

9. The purification system of claim 1 wherein the baffles comprise an opening on one end.

10. The purification system of claim 1 wherein the baffles comprise randomly spaced openings therethrough.

11. The purification system of claim 1 wherein the reaction chamber comprises a mesh disposed therein.

12. A light fixture comprising:
a frame or a structure;
a purification system of claim 1 coupled to the frame or the structure.

13. The light fixture of claim 12 wherein the housing is a replaceable structure that is removably coupled to the frame or the structure.

14. The light fixture of claim 12 further comprising a first deflector removably coupled to the frame or the structure.

15. The light fixture of claim 12 further comprising a second deflector removably coupled to the frame or the structure, said fan and said reaction chamber disposed between the first deflector and the second deflector.

16. A mobile platform comprising:
a base; and
the purification system of claim 1 coupled to the base.

17. The mobile platform of claim 16 further comprising a humidifier coupled to the base.

18. The mobile platform of claim 16 wherein the mobile platform is autonomous.

19. The mobile platform of claim 16 wherein the surface, the light source and the fan are disposed in the reaction chamber.

20. The mobile platform of claim 16 wherein the reaction chamber comprises an air outlet having a filter disposed adjacent thereto.

21. A purification system comprising:
a housing having a lateral direction and a longitudinal direction;
a reaction chamber coupled to the housing comprising an inlet and an outlet;
a sensor coupled within the reaction chamber;
a fan coupled to the inlet of the reaction chamber communicating air through the reaction chamber to the outlet;
a dose control circuit board coupled to the outlet, said dose control circuit board comprising light sources having a first wavelength directed at air passing through the reaction chamber, said dose control circuit board comprising passages therethrough;

a plurality of baffles each comprising a parabolic portion having a curved surface with a photocatalyst;

the reaction chamber comprising a plurality of flow cavities extending across the reaction chamber in the lateral direction defined by the plurality of baffles disposed within the reaction chamber;

a fan coupled to the reaction chamber communicating air through the reaction chamber and the flow cavities therein;

a plurality of light sources, each light source associated with a respective one of the plurality of baffles so that each light source is positioned in each flow cavity at an intersection of the respective baffle and the housing having a first wavelength and each light source generating generate light directed at the surface of the parabolic portion having the photocatalyst so that light reflected from the parabolic portion is directed in a parallel direction within the flow cavities and laterally within the flow cavities and at air passing laterally through the flow cavities in a direction of the air within the flow cavities; and a controller programmed to control a fan speed based on a sensor signal from the sensor within the reaction chamber to control a dose of light from the light.

22. The purification system of claim 21 wherein the sensor comprise a temperature sensor and the sensor signal comprise a temperature signal.

23. The purification system of claim 21 wherein the sensor comprise a pressure sensor and the sensor signal comprise a pressure signal.

24. The purification system of claim 21 wherein the sensor comprise a flow sensor and the sensor signal comprise a flow signal.

25. The purification system of claim 21 wherein the sensor comprises a temperature sensor and a flow sensor and the sensor signal comprises a temperature signal and a flow signal.

26. The purification system of claim 21 wherein the passages comprise thermal vias.

27. The purification system of claim 21 wherein the passages comprise openings coupled to a door and further comprising a controller programmed to control a damper actuator coupled to the door based on a sensor signal from a sensor within the reaction chamber.

* * * * *